(12) United States Patent
Pike et al.

(10) Patent No.: US 7,029,657 B2
(45) Date of Patent: Apr. 18, 2006

(54) NASAL SPRAY STEROID FORMULATION AND METHOD

(75) Inventors: Malcolm C. Pike, Marina Del Rey, CA (US); Darcy V. Spicer, La Canada, CA (US); AnnaMarie Daniels, Pacific Palisades, CA (US); John R. Daniels, Pacific Palisades, CA (US)

(73) Assignee: Balance Pharmaceuticals, Inc., Santa Monica, CA (US)

( * ) Notice: Subject to any disclaimer, the term of this patent is extended or adjusted under 35 U.S.C. 154(b) by 176 days.

(21) Appl. No.: 10/295,337

(22) Filed: Nov. 15, 2002

(65) Prior Publication Data

US 2004/0022738 A1 Feb. 5, 2004

Related U.S. Application Data

(60) Provisional application No. 60/400,576, filed on Aug. 2, 2002.

(51) Int. Cl.
*A61K 9/12* (2006.01)
*A61K 9/72* (2006.01)

(52) U.S. Cl. .................. 424/45; 424/434; 424/426; 424/239; 514/2; 514/841; 514/843; 514/874

(58) Field of Classification Search ............... 424/434, 424/45, 239, 426; 514/2, 841, 843, 874
See application file for complete search history.

(56) References Cited

U.S. PATENT DOCUMENTS

| | | | |
|---|---|---|---|
| 4,315,925 A | 2/1982 | Hussain et al. | |
| 4,383,993 A | 5/1983 | Hussain et al. | |
| 4,476,116 A | 10/1984 | Anik | |
| 4,596,795 A | 6/1986 | Pitha | |
| 4,659,696 A | 4/1987 | Hirai et al. | |
| 4,724,064 A | 2/1988 | Reid | |
| 5,089,482 A | 2/1992 | Hermens et al. | |
| 5,116,817 A | 5/1992 | Anik | |
| 5,130,137 A | 7/1992 | Crowley, Jr. | |
| 5,211,952 A | 5/1993 | Spicer et al. | |
| 5,296,468 A | 3/1994 | Hoeger et al. | |
| 5,340,584 A | 8/1994 | Spicer et al. | |
| 5,340,585 A | 8/1994 | Pike et al. | |
| 5,340,586 A | 8/1994 | Pike et al. | |
| 5,681,817 A | 10/1997 | Hodgen et al. | |
| 5,955,454 A | 9/1999 | Merkus | |
| 5,977,070 A | 11/1999 | Piazza et al. | |
| 6,225,298 B1 | 5/2001 | Spicer et al. | |
| 2001/0016578 A1 | 8/2001 | Spicer et al. | |

FOREIGN PATENT DOCUMENTS

| | | |
|---|---|---|
| EP | 0 709 099 A2 | 5/1996 |
| EP | 0 538 443 B1 | 10/1997 |
| WO | WO 92/01440 | 2/1992 |
| WO | WO 92/18107 | 10/1992 |
| WO | WO 94/26207 | 11/1994 |
| WO | WO 94/26208 | 11/1994 |
| WO | WO 96/15794 | 5/1996 |

OTHER PUBLICATIONS

Hermens, W., et al., *Pharmaceutical Research* 7(5):500-503, (1990).
Hermens, W., *Pharmaceutisch Weekblad Scientific Edition* 14(4A): 253-257, (1992).
Sugimoto, A.K., et al., *Fetrility and Sterility* 60(4):672-674, (1993).

*Primary Examiner*—Sreeni Padmanabhan
*Assistant Examiner*—Mina Haghighatian
(74) *Attorney, Agent, or Firm*—Judy M. Mohr; Perkins Coie LLP (57) ABSTRACT

The present invention relates to an improvement in a method of contraception, in treatment of benign gynecological disorders, and in hormone replacement. The improved method includes administering intranasally an estrogenic compound and an androgenic compound, and in some embodiments an optional progestin compound, in a once-daily bolus formulation comprised of the two or three steroids complexed with a cyclodextrin. An intranasal delivery system for administration of the formulation is also described.

10 Claims, 1 Drawing Sheet

Fig. 1

NASAL SPRAY STEROID FORMULATION AND METHOD

This application claims the benefit of U.S. Provisional Application No. 60/400,576, filed Aug. 2, 2002, incorporated herein by reference in its entirety.

FIELD OF THE INVENTION

The present invention relates to an improvement in a method of contraception or in treatment of benign gynecological disorders in conjunction with a GnRH compound, or in hormone replacement for postmenopausal or surgically postmenopausal women where an estrogenic compound and an androgenic compound and, optionally, a progestin compound are administered. The improvement involves administering the estrogenic compound and the androgenic compound and, optionally, a progestin compound intranasally in a once-daily bolus of a formulation comprised of the two or three steroids complexed with a cyclodextrin.

BACKGROUND OF THE INVENTION

During a woman's reproductive life, a delicate and complex interplay of hormones are timed and controlled by the hypothalamus. The hormones that participate in the feedback system regulating the menstrual cycle include estrogens and progesterone, the pituitary gonadotropins FSH (follicle stimulating hormone) and LH (luteinizing hormone), and gonadotropin-releasing hormone (GnRH) from the hypothalamus.

Manipulation of the hormonal balance is a recognized approach of contraception and of treatment of benign gynecological disorders. In particular, administration of a GnRH compound for contraception has been described (U.S. Pat. Nos. 5,340,584; 5,211,952). Typically, the GnRH compound is administered in a slow or controlled-release fashion for continuous suppression of ovarian estrogen and progesterone production. Estrogen, often a progestin, and sometimes an androgen, are "added-back" to ameliorate the effects of hormonal deficiency. The hormone add-backs are also often administered in a slow, controlled-release or time-release fashion to maintain a constant hormonal serum level.

Treatment of benign gynecological disorders by administration of a GnRH compound has also been described (U.S. Pat. Nos. 5,340,584; 5,340,585; 5,681,817). During a women's reproductive years, defined as the time between onset of menses (menarche) and the final episode of bleeding (menopause), that is a premenopausal woman, a variety of benign gynecological disorders can occur. Common benign gynecological disorders include, but are not limited to, premenstrual syndrome, endometriosis, uterine leiomyomata (uterine fibroids), and polycystic ovarian syndrome. As for contraceptive use, a GnRH compound is administered to suppress ovarian follicle development and sex steroid production, and for benign gynecologic disorders, to relieve or treat symptoms associated with the disorder.

A woman's endogenous level of estrogen is significantly reduced upon entering menopause or upon premature surgical menopause induced by removal of the ovaries. The amount of a woman's endogenous estrogen is typically reduced to less than about 10% to about 20% of premenopausal levels following natural or surgical menopause. This reduction of endogenous estrogen levels results in the loss of estrogen's health protective effects, particularly with respect to bone mineral density. Estrogen replacement therapy (ERT) is often utilized as a treatment to increase the level of estrogen in women having reduced levels of endogenous estrogen resulting from natural or surgical menopause. Supplemental estrogen is provided to the women in order to inhibit, ameliorate, or prevent diseases or conditions which result from the reduction of endogenous estrogen.

The administration of drugs by absorption through mucosae, such as the nasal mucosa or vaginal mucosa, has been of considerable interest in recent years. This route of drug delivery is an alternative to oral administration in cases where drugs are poorly absorbed or are extensively metabolized in the gastrointestinal tract or subjected to first-pass metabolism in the liver. In particular, nasal mucosa has the desirable properties of being highly vascular leading to rapid uptake and of avoidance of first-pass metabolism in the liver, since the venous system from the nose passes directly into the systemic circulatory system. The nasal mucosa also exhibits moderate permeability to water-soluble compounds, comparable to that of the ileum. The permeability of nasal mucosa is higher for most compounds than other mucosa, due in part to the difference in structure of the cells lining the body cavities.

Efficiency of delivery of drugs by an intra-nasal route is influenced by the degree and rapidity of enzymatic degradation, the nasal clearance rate, as well as the drug's permeability through the mucosa. The clearance rate is produced by the coordinated movement of cilia and is known to be highly dependent upon the prevailing physiological and pathological conditions. Thus, for many drugs administration intranasally is inefficient due to low uptake of the drug, hence low bioavailability.

Another potential problem associated with intranasal delivery is mucosal irritation. Irritation caused by the drug itself and/or by absorption or penetration promoters or enhancers often limits the success of nasal formulations. Chronic administration of irritating nasal formulations can cause necrosis, inflammation, exudation, removal of the epithelial monolayer or can lead to irreversible damage to the nasal mucosa.

Nasal formulations for delivery of female sex hormones have been described (see, for example, U.S. Pat. Nos. 4,596,795; 5,089,482). However, formulations comprised of an estrogenic compound and an androgenic compound such as testosterone that are therapeutically effective when delivered intranasally and that are sufficiently non-irritating to the nasal mucosa for commercial viability have not been described.

SUMMARY OF THE INVENTION

Accordingly, it is an object of the invention to provide a nasal preparation having an estrogenic compound and an androgenic compound and, an optional progestin compound, in the form of a complex with a cyclodextrin.

It is another object of the invention to provide a bolus-form of delivery of a composition comprised of an estrogenic compound and an androgenic compound and, optionally a progestin compound, that offers a therapeutic activity similar to that of a slow-release composition of the same active agents, with similar hormonal areas under the curves (AUCs) in a concentration-time plot of the two formulations or in achieving a similar biological effect such as amelioration of symptoms related to sex-steroid deprivation, specifically, loss of bone mineral density, atrophic vaginitis, and vasomotor instability.

In one aspect, the invention includes improvements in methods for contraception, for treatment of benign gynecological disorders, both in conjunction with a GnRH compound, and for hormone replacement for post-menopausal or surgically-postmenopausal women, where an estrogenic compound and an androgenic compound, such as testosterone, and an optional progestin compound, are administered, often on a long-term basis of longer than about 6 to about 12 months. The improvement comprises administering the estrogenic compound and the androgenic compound (an the optional progestin compound when present) intranasally in a once-daily bolus of an aqueous formulation containing the two or three compounds in the form of soluble complexes with a cyclodextrin. The amount of the two or three compounds administered is such as to produce estrogen and androgen and, optionally, progestin serum concentrations levels having substantially the same area-under-the-curve concentrations as are produced when therapeutically effective doses of the two or three compounds are administered transdermally. That is, administration of the estrogenic compound and the androgenic compound and, optionally, a progestin compound intranasally in bolus form achieves the same desired biological effect as that produced when the two or three compounds are administered transdermally.

The method of the invention, when used for treatment of a benign gynecological disorder or for contraception in conjunction with a GnRH compound, in one embodiment, includes administering the GnRH compound by any suitable route of administration, which may be different than an intranasal route employed for administration of the estrogenic compound and the androgenic compound and, optionally a progestin compound. The GnRH compound can be administered simultaneously or sequentially.

In one embodiment, the cyclodextrin is 2-hydroxypropyl-β-cyclodextrin and is present at a concentration between about 50 mg/mL and 300 mg/mL. In another embodiment, 2-hydroxypropyl-β-cyclodextrin has a degree of substitution of between 2 and 8, more preferably between 5 and 8.

In another embodiment, the estrogenic compound is 17β-estradiol and the androgenic compound is testosterone and together they have a combined molar occupancy with respect to the cyclodextrin that is greater than the molar occupancy achievable with either steroid alone. For example, the combined molar occupancy of the two steroids is greater than 50%, in one embodiment. In another embodiment, the combined molar occupancy of the two steroids is greater than 60%.

In another embodiment, the estrogenic compound is 17β-estradiol at a daily dose between 0.15 mg and 0.6 mg and the androgenic compound is testosterone at a daily dose between 0.15 mg and 1 mg.

The mole ratio of 17β-estradiol to testosterone is between 1:1 and 1:2, in some embodiments.

In yet other embodiments, the molar occupancies of 17β-estradiol and testosterone are greater than 20% and 40%, respectively.

In another aspect, the invention includes an intranasal drug-delivery system for use in contraception or in treatment of benign gynecological disorders in conjunction with a GnRH compound, or in hormone replacement for postmenopausal or surgically postmenopausal women. The system is comprised of (a) a nasal-spray nebulizer effective to deliver a spray volume of between about 30 to about 200 μL, and (b) contained in the nebulizer, a drug formulation containing an estrogenic compound and an androgenic compound such as testosterone and, optionally, a progestin compound in an aqueous medium, in solubilized form complexed with a cyclodextrin. The amount of the two or three compounds administered in the spray volume is such as to produce estrogen and androgen, and progestin when present, serum concentrations having substantially the same area-under-the-curve concentrations as those produced when therapeutically effective doses of the two or three compounds are administered transdermally. That is, the biological effect achieved by intranasal administration of the two or three compounds is comparable to that produced when the two or three compounds are administered transdermally.

In one embodiment, the nasal preparation and the system are used on a long-term basis, i.e., for longer than about 6 months, more preferably for longer than about 12 months.

In yet another aspect, the invention includes a method of formulating two or more different steroids in a water-soluble form suitable for uptake by a human subject through mucosal tissue. The method is comprised of forming an aqueous solution of a cyclodextrin and adding the first, second and, optionally, third steroid to the solution in amounts effective to achieve a combined molar occupancy of the two or three steroids which is greater than the molar occupancy achievable with any single steroid alone.

In one embodiment, the aqueous solution of cyclodextrin is heated to above about 70° C. prior to said adding, and the solution is cooled slowly after solubilization of the added steroids.

In another embodiment, the first steroid is added to the solution until a maximum or near-maximum molar occupancy is reached, then the second and, optionally a third steroid, is/are added until a combined maximum or near-maximum molar occupancy is reached.

The cyclodextrin can be 2-hydroxypropyl-β-cyclodextrin, the estrogenic compound can be 17β-estradiol, the second steroid can be testosterone, and the third steroid can be progesterone.

These and other objects and features of the invention will be more fully appreciated when the following detailed description of the invention is read in conjunction with the accompanying examples and drawings.

DETAILED DESCRIPTION OF THE INVENTION

I. Nasal Formulation for Use in the Method

As noted above, the invention includes a nasal preparation for use in a variety of treatment modalities. For example, the nasal preparation finds use as add-back hormone replacement in women who have hormone production suppressed with a gonadotropin releasing hormone (GnRH) compound. "GnRH compound" refers to peptide and non-peptide GnRH analogs, including agonists and antagonists. These compounds are administered, for example, for female contraception and in the treatment of benign gynecological disorders. Thus, women currently taking a GnRH compound for treatment of a benign gynecological disorder or for contraception are candidates for treatment with the nasal preparation described herein. The nasal preparation also is suitable for use in hormone replacement therapy for both postmenopausal and surgically postmenopausal women. The nasal preparation is also suitable in peri-menopausal women, i.e., women entering menopause who have a low hormone level, and in women with a low hormone level as a result of another condition, disorder, or treatment regimen. The nasal preparation suitable for these various situations and conditions will now be described.

A1. Composition Components: Estrogenic Compound

The composition for use in the method of the invention includes an estrogenic compound. The estrogenic compound is effective to prevent one or more of the clinically recognized symptoms or signs of estrogen deficiency, including but not limited to bone loss, vaginal atrophy, and hot flashes.

The estrogenic compound can be a single-component natural or synthetic estrogen composition, or a combination of such compounds. As used herein, the term "estrogenic compound" refers to both natural and synthetic materials having activity to mitigate the signs and symptoms of estrogen deficiency. Natural and synthetic estrogenic compositions which can be used according to the invention described herein include natural estrogenic hormones and congeners, including but not limited to estradiol, estradiol benzoate, estradiol cypionate, estradiol valerate, estrone, diethylstilbestrol, piperazine estrone sulfate, ethinyl estradiol, mestranol, polyestradiol phosphate, estriol, estriol hemisuccinate, quinestrol, estropipate, pinestrol, and estrone potassium sulfate. Equine estrogens, such as equilelinin, equilelinin sulfate, and estetrol, and synthetic steroids combining estrogenic, androgenic, and progestogenic properties such as tibolone may also be employed.

Typical dose ranges for estrogenic compounds depend on the compound and on the characteristics of the patient. For an adult human female patient treated with a transdermal 17β-estradiol preparation, a typical dose range is one that maintains a serum level of estradiol of about 25 pg/mL to about 140 pg/mL, more preferably between about 30 pg/mL to about 50 pg/mL. A specific example of a composition containing an estrogenic compound is one comprised of 17β-estradiol and testosterone. The two compounds, along with other optional excipients, are formulated for delivery intranasally. For an intranasal preparation, a preferred dosage range for 17β-estradiol is between about 0.15 mg and 0.6 mg.

A2. Composition Components: Androgenic Compound

The composition further includes an androgenic compound. The androgenic compound is in an amount effective to increase a patient's androgen level to a level not exceeding a "normal" premenopausal level, and in particular in concert with the estrogenic composition to maintain bone mineral density. Such "normal" androgen levels are on the order of about 15 ng/dL to about 80 ng/dL for testosterone.

Suitable androgenic compounds for use in the composition include but are not limited to testosterone, androstenedione, dihydrotestosterone, testosterone propionate, testosterone enanthate, testosterone cypionate, methyltestosterone, danazol, dromostanolone propionate, ethylestrenol, methandriol, nandrolone decanoate, nandrolone phenpropionate, oxandrolone, oxymethalone, and stanozolol.

Typical dose ranges for androgenic hormones depend upon the choice of compound and the individual patient. For an adult human female administered testosterone, typical doses are administered to provide serum levels of testosterone of from about 15 ng/dL to about 80 ng/d, and preferably about 40 ng/dL to about 60 ng/dL. For an intranasal preparation, a typical daily dose can range from between about 0.15 mg to about 1 mg. The steroid compounds, along with other optional excipients, are formulated for delivery intranasally, and exemplary formulations are described below.

A3. Composition Components: Cyclodextrin Excipient

In a preferred embodiment, an absorption-promoting component is included. Exemplary absorption promoting components include surfactant acids, such as cholic acid, glycocholic acid, taurocholic acid, and other cholic acid derivatives, chitosan and cyclodextrins. In a preferred embodiment, a cyclodextrin is included in the preparation. Cyclodextrins are cyclic oligosaccharides of α-D-glucopyranose and can be formed by the catalytic cyclization of starch. Due to a lack of free rotation about the bonds connecting the glycopyranose units, cyclodextrins are toroidal or cone shaped, rather than cylindrical. The cyclodextrins have a relatively hydrophobic central cavity and a hydrophilic outer surface. The hydrophobic cage-like structure of cyclodextrins has the ability to entrap a variety of guest compounds to form host-guest complexes in the solid state and in solution. These complexes are often termed inclusion complexes and the guest compounds are released from the inclusion site.

The most common cyclodextrins are α-, β-, and γ-cyclodextrin, which consist of 6, 7, or 8 glucopyranose units, respectively. Cyclodextrins containing 9, 10, 11, 12, and 13 glucopyranose units are designated δ-, ε-, ξ-, η-, and θ-cyclodextrin, respectively. Characteristics of α-, β-, γ-, and δ-cyclodextrin are shown in Table 1.

TABLE 1

| Cyclodextrin Characteristics | | | | |
| --- | --- | --- | --- | --- |
| | α-cyclodextrin | β-cyclodextrin | γ-cyclodextrin | δ-cyclodextrin |
| no. of glucopyranose units | 6 | 7 | 8 | 9 |
| molecular weight (Daltons) | 972 | 1135 | 1297 | 1459 |
| central cavity diameter (Å) | 4.7–5.3 | 6.0–6.5 | 7.5–8.3 | 10.3–11.2 |
| water solubility (at 25° C., g/100 mL) | 14.5 | 1.85 | 23.2 | 8.19 |

Derivatives formed by reaction with the hydroxyl groups lining the upper and lower ridges of the toroid are readily prepared and offer a means of modifying the physicochemical properties of the parent cyclodextrins. The parent cyclodextrins, and in particular β-cyclodextrin, have limited aqueous solubility. Substitution of the hydroxyl groups, even with hydrophobic moieties such as methoxy and ethoxy moieties, typically increases solubility. Since each cyclodextrin hydroxyl group differs in chemical reactivity, reaction with a modifying moiety usually produces an amorphous mixture of positional and optical isomers. The aggregate substitution that occurs is described by a term called the degree of substitution. For example, a 2-hydroxypropyl-β-cyclodextrin with a degree of substitution of five would be composed of a distribution of isomers of 2-hydroxypropyl-β-cyclodextrin in which the average number of hydroxypropyl groups per 2-hydroxypropyl-β-cyclodextrin molecule is 5. Degree of substitution can be determined by mass spectrometry or nuclear magnetic resonance spectroscopy. These methods do not give information as to the exact location of the substituents (C1, C2, C3, etc.) or the distribution of the substituents on the cyclodextrin molecule (mono, di, tri, poly). Theoretically, the maximum degree of substitution is 18 for α-cyclodextrin; 21 for β-cyclodextrin; and 24 for γ-cyclodextrin, however, substituents with hydroxyl groups present the possibility for additional hydroxylalkylations.

The cyclodextrin used in the present invention is preferably an α-, β-, or γ-cyclodextrin. The cyclodextrin is selected for use depending on which cyclodextrin binds the guest compounds and yields the desired bioavailability. In a preferred embodiment, a derivative of a cyclodextrin is selected, and derivatives such as hydroxypropyl, dimethyl, and trimethyl substituted cyclodextrins are contemplated, as are cyclodextrins linked with sugar molecules, sulfonated cyclodextrins, carboxylated cyclodextrins, and amino derivatives such as diethylamino cyclodextrins. In a preferred embodiment, the cyclodextrin is a β-cyclodextrin, and in a more preferred embodiment, the cyclodextrin is 2-hydroxypropyl-β-cyclodextrin. In yet another embodiment, the 2-hydroxypropyl-β-cyclodextrin has a degree of substitution between 2 and 8, more preferably between 4 and 8, most preferably between 5 and 8. Exemplary formulations that include the cyclodextrin 2-hydroxypropyl-β-cyclodextrin are described below.

A4. Composition Components: Progestin Compound

The composition comprised of an estrogenic compound and an androgenic compound can optionally include a progestin. Formulations that include a progestin can be administered for a limited period of time, for example on the order of 5 to 20 days, and preferably 10 to 15 days after each extended treatment regimen with a composition comprised of an estrogenic compound and an androgenic compound. The extended treatment regimen, during which the estrogenic and androgenic compounds are administered, is typically for at least about 4 months, more preferably for greater than about 6 months, and more specifically, of from about 4 months to about 12 months. The progestin is provided for a limited time period after such an extended time period. The progestin is given in an amount effective to minimize or eliminate the occurrence of endometrial hyperplasia or to preserve the efficacy achieved with hormone suppression by GnRH compounds in certain benign gynecologic disorders such as endometriosis and uterine fibroids by substantially reducing the possibility of endometrial hyperstimulation which may occur during prolonged treatment with estrogenic steroids without a progestin.

Suitable progestational agents (progestins) include but are not limited to dydrogesterone, ethynodiol diacetate, hydroxyprogesterone caproate, medroxyprogesterone acetate, norethindrone, norethindrone acetate, norethynodrel, norgestrel, progesterone, and megestrol acetate. Typical dose ranges for progestins depend upon the choice of steroid and the individual patient. Doses are selected as adequate to produce a secretory uterine endothelium after the time interval of progestin treatment (about 5 to about 20 contiguous days, and preferably about 10 to about 15 contiguous days). The serum level of progesterone is generally less than about 50 ng/dL after the time interval of progestin treatment.

B. Exemplary Nasal Preparations

As noted above, the composition comprised of an estrogenic compound and an androgenic compound and, optionally, a progestin compound complexed with a cyclodextrin are mucosally administered by contacting the composition in a suitable dosage form with mucosal tissue of the vagina, nose, rectum, or mouth. In a preferred embodiment, the composition is administered via the nasal mucosa, i.e., intranasally. The nasal mucosa provides a useful anatomical site for systemic delivery. The nasal tissue is highly vascularized, providing an attractive site for rapid and efficient absorption. The adult nasal cavity has a capacity of around 20 mL, with a large surface area of approximately 180 cm$^2$ for drug absorption, due in part to the microvilli present along the psuedostratified columnar epithelial cells of the nasal mucosa.

A nasal preparation comprised of the composition described above can take a variety of forms for administration in nasal drops, nasal spray, gel, ointment, cream, powder or suspension, using a dispenser or other device as needed. A variety of dispensers and delivery vehicles are known in the art, including single-dose ampoules, atomizers, nebulizers, pumps, nasal pads, nasal sponges, nasal capsules, and the like.

More generally, the preparation can take a solid, semi-solid, or liquid form. In the case of a solid form, the components may be mixed together by blending, tumble mixing, freeze-drying, solvent evaporation, co-grinding, spray-drying, and other techniques known in the art. Such solid state preparations preferably provide a dry, powdery composition with particles in the range of between about 20 to about 500 microns, more preferably from 50 to 250 microns, for administration intranasally.

A semi-solid preparation suitable for intranasal administration can take the form of an aqueous or oil-based gel or ointment. For example, the components described above can be mixed with microspheres of starch, gelatin, collagen, dextran, polylactide, polyglycolide, or other similar materials that are capable of forming hydrophilic gels. The microspheres can be loaded with drug, and upon administration form a gel that adheres to the nasal mucosa.

In a preferred embodiment, the nasal preparation is in liquid form, which can include an aqueous solution, an aqueous suspension, an oil solution, an oil suspension, or an emulsion, depending on the physicochemical properties of the composition components. The liquid preparation is administered as a nasal spray or as nasal drops, using devices known in the art, including nebulizers capable of delivering selected volumes of formulations as liquid-droplet aerosols. For example, a commercially available spray pump with a delivery volume of 50 μL or 100 μL is available from, for example, Valois (Congers, N.Y.) with spray tips in adult size and pediatric size. In one embodiment, the composition comprised of an estrogenic compound and testosterone are co-administered intranasally via an aerosol spray in a daily volume of between about 10 to 500 μL, more preferably between about 30 to about 200 μL.

The liquid preparation can be produced by known procedures. For example, an aqueous preparation for nasal administration can be produced by dissolving, suspending, or emulsifying the steroid compounds in water, buffer, or other aqueous medium, or in a oleaginous base, such as a pharmaceutically-acceptable oil like olive oil, lanoline, silicone oil, glycerine fatty acids, and the like.

It will be appreciated that excipients necessary for formulation, stability, and/or bioavailability can be included in the preparation. Exemplary excipients include sugars (glucose, sorbitol, mannitol, sucrose), uptake enhancers (chitosan), thickening agents and stability enhancers (celluloses, polyvinyl pyrrolidone, starch, etc.), buffers, preservatives, and/or acids and bases to adjust the pH, and the like.

In a study performed in support of the invention, the solubility of the steroids 17β-estradiol and testosterone, alone and in combination, in varying concentrations of 2hydroxypropyl-β-cyclodextrin was determined. As described in Example 1, defined amounts of each steroid were added to 1 mL of 2-hydroxypropyl-β-cyclodextrin in water. The solubility of the steroids was determined, and the results are shown in Tables 2A and 2B.

Table 2A shows the solubility of 17β-estradiol and testosterone individually in aqueous solutions of 2-hydroxypropyl-β-cyclodextrin. The last two columns in the Table 2A show the molar ratio of each steroid to the cyclodextrin. The molar occupancy of 17β-estradiol with respect to 2-hydroxypropyl-β-cyclodextrin averages approximately 0.21. The molar occupancy of testosterone with respect to 2-hydroxypropyl-β-cyclodextrin averages approximately 0.39.

TABLE 2A

Solubility of 17β-Estradiol and Testosterone as Single Agents in 2-Hydroxypropyl-β-cyclodextrin

| HPβCD* (mg/mL) | 17β-Estradiol solubility (mg/mL) | Testosterone solubility (mg/mL) | Molar Ratio Estradiol/HPβCD | Testosterone/ HPβCD |
|---|---|---|---|---|
| 10 | 0.414 | 0.810 | 0.21 | 0.39 |
| 40 | 1.605 | 2.541 | 0.20 | 0.30 |
| 70 | 2.763 | 5.626 | 0.20 | 0.38 |
| 100 | 4.062 | 6.819 | 0.21 | 0.33 |
| 130 | 5.494 | 11.649 | 0.21 | 0.43 |
| 160 | 6.841 | 13.866 | 0.22 | 0.41 |
| 190 | 8.379 | 16.522 | 0.22 | 0.42 |
| 220 | 9.33 | 18.604 | 0.21 | 0.40 |
| 250 | 11.031 | 21.684 | 0.22 | 0.41 |

*2-hydroxy-propyl-β-cyclodextrin

Table 2B shows the solubility of 17β-estradiol as a first steroid and testosterone as a second steroid in aqueous 2-hydroxypropyl-β-cyclodextrin. The last three columns show the molar ratios of each steroid individually in the 2-hydroxypropyl-β-cyclodextrin solution and of the two steroids together in the solution. The data show that the combined molar occupancy of the two steroids together, average approximately 0.48, is greater than the molar occupancy achieved with either steroid alone (Table 2A).

TABLE 2B

Molar Occupancy of 17β-Estradiol and Testosterone in Sequential Combination in 2-Hydroxypropyl-β-cyclodextrin

| HPβCD* | 17β-Estradiol and Testosterone solubility (mg/mL) | | Molar Ratio | | |
|---|---|---|---|---|---|
| (mg/mL) | Estradiol | Testosterone | Estradiol/ HPβCD | Testosterone/ HPβCD | Estradiol & Testosterone/ HPβCD |
| 10 | 0.164 | 0.658 | 0.08 | 0.31 | 0.40 |
| 40 | 0.834 | 2.819 | 0.11 | 0.34 | 0.44 |
| 70 | 1.562 | 5.073 | 0.11 | 0.35 | 0.46 |
| 100 | 2.157 | 7.113 | 0.11 | 0.34 | 0.45 |
| 130 | 3.202 | 10.552 | 0.12 | 0.39 | 0.51 |
| 160 | 4.053 | 13.422 | 0.13 | 0.40 | 0.53 |
| 190 | 4.796 | 15.742 | 0.13 | 0.40 | 0.52 |
| 250 | 5.774 | 19.986 | 0.12 | 0.38 | 0.50 |

*2-hydroxypropyl-β-cyclodextrin

Figure 1:
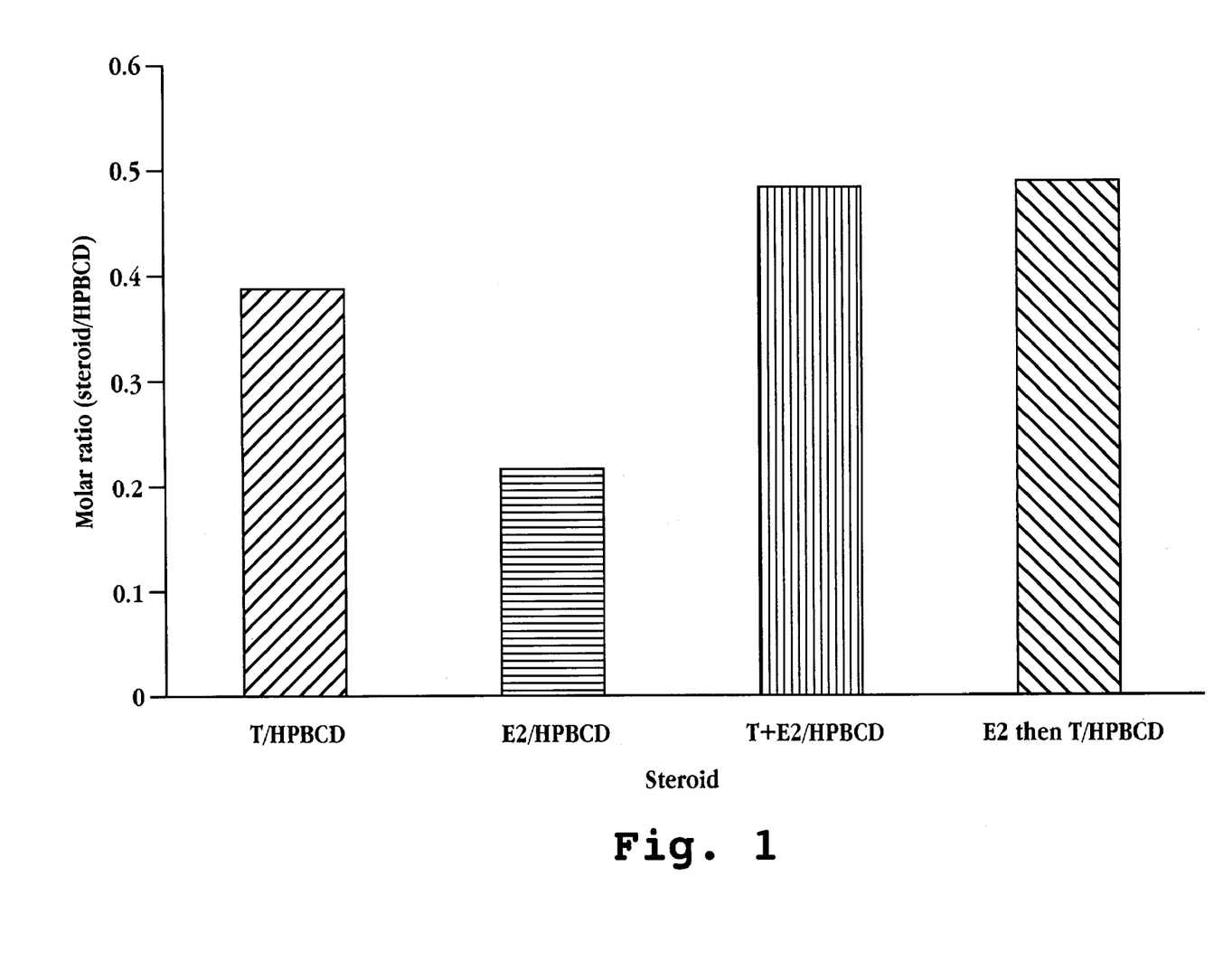
FIG. 1 is a bar graph showing the molar ratio of steroid to 2-hydroxypropyl-62-cyclodextrin for testosterone (T/HPβCD), for 17β-estradiol (E2/HPβCD), and for testosterone and 17β-estradiol in combination where the two steroids are added to the to 2-hydroxypropyl-β-cyclodextrin solution simultaneously (T+E2/HPβCD) or added sequentially (E2 then T/HPβCD).

The molar ratio data of Tables 2A and 2B are presented graphically in FIG. 1. FIG. 1 is a bar graph showing the molar ratio of steroid to 2-hydroxypropyl-β-cyclodextrin for testosterone, for 17β-estradiol, and for testosterone and 17β-estradiol in combination, as discussed above with respect to Tables 2A and 2B and Example 1. The figure also shows the molar ratio determined in another study where 17β-estradiol was first added to the aqueous 2-hydroxypropyl-β-cyclodextrin solution, followed by addition of testosterone. The molar occupancy of the two steroids in combination is similar, regardless of the sequence of addition of the steroids to the 2-hydroxypropyl-β-cyclodextrin solution.

In another study, the solubility of 17β-estradiol and testosterone, alone and in combination, as a function of degree of substitution of 2-hydroxypropyl-β-cyclodextrin was evaluated. Solutions of 2-hydroxypropyl-β-cyclodextrin with degrees of substitution of 5.5, 6.1, and 6.8 were prepared and the maximum concentration of 17β-estradiol and testosterone that could be solubilized was determined. There was a slight trend for the 2-hydroxypropyl-β-cyclodextrin with a lower degree of substitution to solubilize more steroid.

Accordingly, the invention provides a method for formulating two or more steroids in a water-soluble form suitable for uptake through mucosal tissue of a subject. The selected steroids are added to an aqueous solution of a cyclodextrin simultaneously or sequentially, to achieve a molar occupancy of the steroids that is greater than the molar occupancy of any one of the steroids alone. The invention contemplates selection of an estrogenic compound, an androgenic compound, and/or a progestin compound as suitable steroids. When the steroids are added sequentially, the first steroid is added in an amount sufficient to reach a maximum or near-maxiumu molar occupancy of the steroid in the cyclodextrin. Then the second steroid is added in an amount sufficient to reach the combined maximum or near-maxiumum molar occupancy of the steroids in the cyclodextrin. In preparing the formulation, the solution of cyclodextrin can be heated prior to adding the steroids, and heating to above about 70° C. is usually suitable to enhance solubilization if needed. After addition of the two or more steroids the solution can also be slowly cooled.

C. In Vivo Studies

In a study performed in support of the invention, the average serum concentration over 24 hours resulting from transdermal administration of 17β-estradiol and from intranasal administration of 17β-estradiol were compared. As described in Example 3, test subjects received 17β-estradiol transdermally or intranasally. Transdermal estradiol was administered using a Noven Vivelle® or a Noven Vivelle-dot® transdermal patch, both at dosages of 50 μg/day. The subjects treated intranasally received 350 μg estradiol in a liquid spray delivered once per day. Average concentrations for each of the patient populations were determined from blood samples, and the results are summarized in Table 3.

TABLE 3

Average Estradiol Serum Concentration Over 24 Hours (pg/mL) after Treatment with Transdermal and Intranasal 17β-Estradiol

| Estradiol Dosage Form | Average Serum Concentration over 24 Hours (pg/mL) |
|---|---|
| transdermal, Vivelle ® 50 μg/day patch | 34.4 |
| transdermal, Vivelle-dot ® 50 μg/day patch | 36.8 |
| intranasal, 350 μg/spray | 37.8 |

The average serum estradiol concentration over 24 hours for women receiving estradiol transdermally from the Vivelle® patch was 34.4 pg/mL and from the Vivelle®-dot patch was 36.8 pg/mL. The average estradiol concentration for women treated with intranasal estradiol was 37.8 pg/mL. This study shows that an estrogenic compound administered as an intranasal bolus achieves a 24 hour average serum concentration comparable to that achieved by transdermal administration. Thus, in one embodiment the invention provides a 24 hour average serum concentration of estradiol from an intranasal bolus dose of estradiol that is within (plus or minus) about 10% of the 24 hour average estradiol serum concentration achieved from transdermal estradiol administration. That is, the 24 hour average estradiol serum concentration from intranasal bolus administration of estradiol is at least about 90% of the 24 hour average estradiol serum concentration from transdermal administration of estradiol. This result was surprising since heretofore it was unknown (i) if a bolus dose would achieve efficacious blood concentration and (ii) if a bolus dose would achieve a concentration comparable to that of a controlled-release transdermal dose. The data shows that an intranasal bolus dose of an estrogenic compound achieves a therapeutic blood concentration, and that the concentration is comparable, i.e., is within at least about 10%, to that achieved by transdermal administration of the estrogenic compound. The comparable steroid blood concentrations suggests that the physiologic effect achieved by intranasal administration is comparable to that produced when the estrogenic compound and the androgenic compound are administered transdermally.

Example 4 describes a study performed in support of the invention where the efficacy and biologic equivalence between nasal spray add-back estradiol and transdermal estradiol add-back were evaluated. Women with endometriosis treated with intranasal deslorelin (a GnRH compound) were assigned to one of three methods of estradiol add-back: (1) 50 μg/day estradiol transdermal patch, (2) 300 μg/day intranasal estradiol, or (3) 300 μg/day intranasal estradiol with 275 μg/day intranasal testosterone. Loss of bone mineral density (BMD) is a known side effect of treatment with GnRH compounds. Thus, BMD of the lumbar spine (L1–L4) of the test subjects in Example 4 was obtained by dual-energy X-ray absorptiometry (DEXA) prior to and after six months of treatment. The results are shown in Table 4 as the ratio of BMD at the six month time point ($BMD_{6mo.}$) to the BMD prior to treatment ($BMD_{baseline}$). The BMD of subjects treated with deslorelin alone in another study is also shown in Table 4 for comparison.

TABLE 4

Effect of Add-back 17β-Estradiol on the Ratio of 6 Month BMD to Baseline BMD

|  | Mean | N |
|---|---|---|
| Deslorelin (D) | 0.971 | 36 |
| Deslorelin + Transdermal Estradiol | 0.978 | 5 |
| Deslorelin + Intranasal Estradiol | 0.996 | 7 |
| Desloreoin + Intranasal Estradiol + Testosterone | 0.999 | 8 |

A reduction in loss of BMD by addition of estradiol to deslorelin is apparent, since all subjects treated with estradiol had reduced bone loss. The data also shows that estradiol add-back in the form of an intranasal bolus is at least as effective, and in fact slightly more effective, in preventing loss of BMD than a transdermal estradiol add-back, as observed by comparing the BMD ratios for women receiving estradiol transdermally ($BMD_{6mo.}/BMD_{baseline}$=0.978) and for women receiving estradiol intranasally ($BMD_{6mo.}/BMD_{baseline}$=0.996). Thus, estradiol added-back in the form of an intranasal bolus dose reduces the loss of BMD. A nasal spray preparation comprised of an estrogenic compound, where the preparation has an 24 hour average estrogenic compound serum concentration (AUC) within 10% of the 24 hour average transdermal estrogenic compound serum concentration (Table 3), was at least as effective, and preferably more effective, in preventing loss of BMD than an add-back estrogenic compound in the form of a transdermal patch.

In another study, five women were treated with intranasal testosterone. In this study, 250 μg testosterone was formulated into a nasal preparation that also contained deslorelin and estradiol (similar to the procedure in Example 2). The preparation was administered initially on day one of the study, and then again one week later on day 8 of the study. The average testosterone serum concentrations over 24 hours are shown in Table 5.

TABLE 5

Testosterone: Average Concentration Over 24 Hours After Intranasal Administration of 250 μg

| Subject Number | Treatment Day | Testosterone (average concentration over 24 hours, ng/dL) |
|---|---|---|
| 1 | Day 1 | 26.7 |
|  | Day 2 | 24.1 |
| 2 | Day 1 | 26.7 |
|  | Day 2 | 29.9 |
| 3 | Day 1 | 19.0 |
|  | Day 2 | 17.1 |
| 4 | Day 1 | 18.8 |
|  | Day 2 | 16.5 |
| 5 | Day 1 | 19.1 |
|  | Day 2 | 16.2 |
| Average of both observations in each of the 5 subjects |  | 21.4 |

The average testosterone serum concentration over 24 hours for both doses in the five subjects was 21.4 ng/dL. This concentration is comparable to literature reported AUC values achieved from transdermal administration of testosterone. For example, in Javanbakht et al. (*J. of Clinical Endocrinology and Metabolism*, 85(7):2935 (2000) women wearing a transdermal 300 μg/day testosterone patch for 96 hours had an average serum concentration of 15.8 ng/dL. Thus, the nasal formulation of the present invention, i.e., a bolus dose of testosterone, provides a similar area under the curve as a slow release transdermal formulation, as evidenced by similar average serum concentration values over a 24 hour period of time.

In one embodiment, the intranasal dose of the estrogenic compound achieves a transient serum level outside the serum estradiol level of between about 25 pg/mL to about 140 pg/mL that is typically reported in the literature with a 50 μg/day transdermal patch. Although the serum hormone level resulting from intranasal delivery of the hormone is transiently outside this range a similar beneficial effect is achieved. That is, the biological effect(s) resulting from intranasal delivery of an estrogenic compound is similar to the biological effect associated with a serum estradiol level of between about 25 pg/mL to 140 pg/mL even though the actual transient serum level may be outside this range. Thus, in one embodiment, the invention contemplates administration of an estrogenic compound in an amount sufficient to achieve the beneficial biological effects that are associated with a steady estradiol serum level of between about 25 pg/mL to 140 pg/mL, more preferably between about 30 pg/mL to about 100 pg/mL, most preferably, between about 30 pg/mL to about 50 pg/mL.

Similarly, the transient testosterone serum blood level achieved may be lower or higher than that typically obtained by other routes of administration. However, the physiological beneficial effects achieved by intranasal administration are similar to those obtained from a serum testosterone level of between about 15 ng/dL to about 80 ng/dL, more preferably between about 40 ng/dL to 60 ng/dL.

A comparison of the total area under concentration-time curves (AUC) or average concentrations of serum estradiol and testosterone in subjects treated with intranasal estradiol and testosterone to patients treated with estradiol and testosterone by another route, such as transdermal, provides a basis for determining the biological equivalency of different routes of administration. Where the AUCs or average concentrations are similar, despite different routes of administration or different concentration-time profiles, the biological effect achieved is often similar. Thus, in one embodiment, the invention contemplates achieving by intranasal administration of the disclosed composition an average serum estradiol concentration over 24 hours of between about 25 pg/mL and about 50 pg/mL. The invention further contemplates achieving an average serum testosterone concentration over 24 hours of between about 15 ng/dL and about 40 ng/dL.

In a preferred embodiment, the nasal formulation comprising the estrogenic and androgenic compounds, as first and second steroids, is an aqueous preparation that is administered as a once-daily bolus. As noted above, the preparation can optionally include as a third steroid a progestin compound. The two or three steroids are complexed with a cyclodextrin to form a water-soluble complex.

From the foregoing, it can be seen how various objects and features of the invention are met. Contraception and treatment of benign gynecologic disorders, both in conjunction with a GnRH compound, can be complimented by administration of add-back steroids delivered in the form of an intranasal preparation. Hormone replacement therapy can also be achieved by intranasal delivery of steriods. More specifically, an estrogenic compound and an androgenic compound and, an optional a progestin compound, are complexed with cyclodextrin to form a water-soluble complex of the two or three steroids in the cyclodextrin. The preparation when administered intranasally has minimal, if any, nasal irritation, and achieves a 24 hour serum steroid concentration that is within about 10% of the 24 hour serum steroid concentration observed from transdermal administration of the steroids.

III. EXAMPLES

The following examples further illustrate the invention described herein and are in no way intended to limit the scope of the invention.

Example 1

Solubility of 17β-Estradiol and Testosterone with 2-Hydroxypropyl-β-cyclodextrin in Water The solubility of 17β-estradiol and testosterone in varying concentrations of 2hydroxypropyl-β-cyclodextrin (MW 1380 g/mole; 5.5 degree of substitution) was determined as follows. 10 ng 17β-estradiol (MW 272.39 g/mole) was added to 1 mL of 2-hydroxypropyl-β-cyclodextrin in water, the 2-hydroxypropyl-β-cyclodextrin concentration ranging from 10 to 250 ng/mL. In a second series of vials, 20 ng of testosterone (MW 288.43 g/mole) was added to 1 mL of 2-hydroxypropyl-β-cyclodextrin in water, the 2-hydroxypropyl-β-cydodextrin concentration ranging from 10 to 250 ng/mL. In a third set of vials 10 ng 17β-estradiol and 20 ng testosterone were added to 1 mL of 2-hydroxypropyl-β-cyclodextrin in water, the 2hydroxypropyl-β-cyclodextrin concentration ranging from 10 to 250 ng/mL. The vials were mixed at room temperature for about 1 hour. Aliquots were taken from the supernatant of each vial and assayed for steroid concentration. The results are shown in Tables 2A and 2B.

Example 2

Preparation of Intranasal Formulation

2-Hydroxypropyl-β-cyclodextrin was added to water at a concentration of 240 mg/mL and stirred until dissolved. 17β-estradiol was then added to the water-cyclodextrin solution at a concentration of 1.0 mg/mL. The mixture was stirred until dissolution. Testosterone at a concentration of 5.0 mg/mL was then added, and after stirring to dissolution benzalkonium chloride (0.1 mg/mL), ethylene diamine tetra acetic acid (EDTA; 1 mg/mL), and sorbitol (61.6 mg/mL) were added. The mixture was stirred. The volume was brought to the final desired volume and the pH was adjusted as needed. Table 6 summarizes the preparation components, concentrations, and dosages per 50 μL.

TABLE 6

Components in Exemplary Nasal Preparation

| Component | Concentration (mg/mL) | Dose per 50 μL |
|---|---|---|
| 17β-estradiol | 1.0 | 50 μg |
| Testosterone | 5.0 | 250 μg |
| 2-hydroxypropyl-β-cyclodextrin | 240 | 12 mg |
| Benzalkonium chloride | 0.1 | 5 μg |
| EDTA | 1.0 | 50 μg |
| Sorbitol | 61.6 | 3.1 mg |
| Water, USP | as required | |

Example 3

Comparison of Intranasally and Transdermally Delivered Estradiol

Postmenopausal or surgically-postmenopausal females (n=63) were recruited for participation in the study. Thirty women were selected for treatment with transdermal 17β-estradiol from a Noven Vivelle® 50 μg/day patch. Thirty women were treated with transdermal 17β-estradiol from a Noven Vivelle-dot® 50 μg/day patch. The remaining three women were treated intranasally with a single 100 μL bolus spray containing 350 μg 17β-estradiol per spray. The spray formulation in addition to estradiol was comprised of sorbitol (61.6 mg/mL), EDTA (1.0 mg/mL), benzalkonium chloride (0.1 mg/mL), and 2-hydroxypropyl-β-cyclodextrin (100 mg/mL). Blood samples were drawn at defined intervals for analysis of serum estradiol levels. The average concentration of serum estradiol over 24 hours as pg/mL was determined and the results are shown in Table 3.

Example 4

Intranasal Delivery of GnRH Compound with Transdermal or Intranasal Co-Administration of Estradiol Women with endometriosis treated with intranasal deslorelin (GnRH compound) were assigned to one of three methods of add-back: (1) 50 μg/day estradiol transdermal patch, (2) 300 μg/day intranasal estradiol, or (3) 300 μg/day intranasal estradiol with 275 μg/day intranasal testosterone. Bone mineral density (BMD) of the lumbar spine was obtained by dual-energy X-ray absorptiometry (DEXA) prior to and after six months of drug treatment. BMD changes are shown in Table 4 as the ratio of the 6 month value compared to the baseline value.

Although the invention has been described with respect to particular embodiments, it will be apparent to those skilled in the art that various changes and modifications can be made without departing from the invention.

It is claimed:

1. A method for contraception, for treatment of benign gynecological disorders, or for hormone replacement, comprising,
    administering intranasally a bolus of a formulation comprised of an estrogenic compound and an androgenic compound complexed with a cyclodextrin;
    whereby said intranasal administering of said bolus is effective to achieve a physiologic effect comparable to that produced when the estrogenic compound and the androgenic compound are administered transdermally.

2. The method of claim 1, wherein the cyclodextrin is 2-hydroxypropyl-β-cyclodextrin.

3. The method of claim 2, wherein the 2-hydroxypropyl-β-cyclodextrin has a degree of substitution between 2 and 8.

4. The method of claim 2, wherein the concentration of 2-hydroxypropyl-β-cyclodextrin in the formulation is between 50 mg/mL to 300 mg/mL.

5. The method of claim 2, wherein said estrogenic and androgenic compounds in a solution of the cyclodextrin have a combined molar occupancy of greater than 40%.

6. The method of claim 2, wherein said estrogenic and androgenic compounds in a solution of the cyciodextrin have a combined molar occupancy of greater than 50%.

7. The method of claim 2, wherein the estrogenic compound is 17β-estradiol at a daily dose between 0.15 mg and 0.6 mg and the androgenic compound is testosterone at a daily dose between 0.15 mg and 1 mg.

8. The method of claim 7, wherein the mole ratio of 17β-estradiol to testosterone is between 1:1 and 1:5.

9. The method of claim 7, wherein the molar occupancies of 17β-estradiol and testosterone are greater than 20% and 40%, respectively.

10. The method of claim 1, wherein said formulation further comprises a progestin compound as a third steroid.

* * * * *